US012778689B2

(12) United States Patent
Wenderow et al.

(10) Patent No.: US 12,778,689 B2
(45) Date of Patent: *Nov. 3, 2026

(54) ROBOTIC CATHETER SYSTEM INCLUDING IMAGING SYSTEM CONTROL

(71) Applicant: Corindus, Inc., Newton, MA (US)

(72) Inventors: Tal Wenderow, Newton, MA (US); John Murphy, North Reading, MA (US); David Handler, Newton, MA (US); Nicholas Kottenstette, Sterling, MA (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 252 days.

This patent is subject to a terminal disclaimer.

(21) Appl. No.: 18/331,482

(22) Filed: Jun. 8, 2023

(65) Prior Publication Data

US 2023/0310100 A1 Oct. 5, 2023

Related U.S. Application Data

(63) Continuation of application No. 16/385,398, filed on Apr. 16, 2019, now Pat. No. 11,707,334, which is a (Continued)

(51) Int. Cl.

| | |
|---|---|
| ***A61B 34/30*** | (2016.01) |
| ***A61B 6/00*** | (2024.01) |

(Continued)

(52) U.S. Cl.

CPC ................ *A61B 34/30* (2016.02); *A61B 6/12* (2013.01); *A61B 6/461* (2013.01); *A61B 6/481* (2013.01);

(Continued)

(58) Field of Classification Search

None

See application file for complete search history.

(56) References Cited

U.S. PATENT DOCUMENTS

| | | | |
|---|---|---|---|
| 5,253,169 | A | 10/1993 | Corby |
| 5,278,887 | A | 1/1994 | Chiu |

(Continued)

FOREIGN PATENT DOCUMENTS

| | | |
|---|---|---|
| DE | 102006011255 | 8/2012 |
| EP | 2322088 | 5/2011 |

(Continued)

OTHER PUBLICATIONS

JP-2003110881-A machine translation (Year: 2003).*

International Search Report for PCT Application No. PCT/US2012/030068; received Jul. 13, 2012.

*Primary Examiner* — Christopher Koharski

*Assistant Examiner* — Renee C Langhals

(57) ABSTRACT

A robotic catheter procedure system includes a bedside system and a workstation. The bedside system includes an actuating mechanism configured to engage and to impart movement to a percutaneous device. The workstation includes a user interface and a control system configured to be operatively coupled to the user interface, the bedside system, and a medical imaging system. The control system is responsive to a first input and to a second input, and the user interface receives the second input from a user. The control system is configured to generate a first control signal to the medical imaging system based on the first input, and the medical imaging system captures at least one image in response to the first control signal. The control system is configured to generate a second control signal to the actuating mechanism based on the second input, and the actuating mechanism causes movement of the percutaneous device in response to the second control signal. The first (Continued)

input is indicative of upcoming percutaneous device movement.

29 Claims, 8 Drawing Sheets

Related U.S. Application Data continuation of application No. 15/094,464, filed on Apr. 8, 2016, now Pat. No. 10,299,867, which is a continuation of application No. 13/833,874, filed on Mar. 15, 2013, now Pat. No. 9,320,479, which is a continuation-in-part of application No. PCT/US2012/030068, filed on Mar. 22, 2012.

(60) Provisional application No. 61/466,399, filed on Mar. 22, 2011.

(51) Int. Cl.

| | |
|---|---|
| ***A61B 6/12*** | (2006.01) |
| ***A61B 6/46*** | (2024.01) |
| ***A61B 34/00*** | (2016.01) |
| ***A61B 34/20*** | (2016.01) |
| ***A61B 90/00*** | (2016.01) |

(52) U.S. Cl.

CPC .............. *A61B 6/542* (2013.01); *A61B 6/548* (2013.01); *A61B 34/74* (2016.02); *A61B 90/37* (2016.02); *A61B 6/467* (2013.01); *A61B 2034/2065* (2016.02); *A61B 2034/301* (2016.02); *A61B 2034/742* (2016.02); *A61B 2090/376* (2016.02); *A61B 2090/3784* (2016.02)

(56) References Cited

U.S. PATENT DOCUMENTS

| | | | | |
|---|---|---|---|---|
| 6,135,946 | A * | 10/2000 | Konen | A61B 90/36 600/407 |
| 6,463,121 | B1 | 10/2002 | Milnes | |
| 6,587,709 | B2 | 7/2003 | Solf et al. | |
| 6,726,675 | B1 | 4/2004 | Beyar | |
| 7,403,811 | B2 | 7/2008 | Sathyanarayana | |
| 7,769,427 | B2 | 8/2010 | Shachar | |
| 7,873,402 | B2 | 1/2011 | Shachar | |
| 2003/0069653 | A1 * | 4/2003 | Johnson | A61B 6/467 700/83 |
| 2003/0097062 | A1 | 5/2003 | Toth et al. | |
| 2003/0144590 | A1 | 7/2003 | Maschke | |
| 2003/0220555 | A1 | 11/2003 | Heigl | |
| 2005/0203382 | A1 | 9/2005 | Govari et al. | |
| 2006/0241370 | A1 | 10/2006 | Kramp | |
| 2006/0241413 | A1 | 10/2006 | Boese | |
| 2006/0247520 | A1 | 11/2006 | McGee | |
| 2006/0247521 | A1 * | 11/2006 | McGee | A61B 90/36 600/434 |
| 2007/0123771 | A1 | 5/2007 | Redel et al. | |
| 2007/0135709 | A1 | 6/2007 | Rioux et al. | |
| 2007/0185486 | A1 | 8/2007 | Hauck et al. | |
| 2007/0195927 | A1 * | 8/2007 | Fung | G01N 23/043 378/58 |
| 2007/0197896 | A1 * | 8/2007 | Moll | A61B 34/20 600/407 |
| 2008/0097195 | A1 | 4/2008 | Urquhart et al. | |
| 2008/0118023 | A1 * | 5/2008 | Besson | A61B 6/4216 604/510 |
| 2008/0292056 | A1 * | 11/2008 | Marar | A61B 6/467 378/98 |
| 2010/0069833 | A1 * | 3/2010 | Wenderow | A61B 17/00234 604/95.01 |
| 2010/0073150 | A1 | 3/2010 | Olson et al. | |
| 2010/0094124 | A1 | 4/2010 | Schoonenberg et al. | |
| 2010/0272238 | A1 | 10/2010 | Machan et al. | |
| 2011/0015569 | A1 | 1/2011 | Kirschenman et al. | |
| 2013/0163721 | A1 | 6/2013 | Koh | |

FOREIGN PATENT DOCUMENTS

| | | | | |
|---|---|---|---|---|
| EP | 1421913 | | 4/2012 | |
| JP | 2003110881 | A * | 4/2003 | |
| WO | 2010025338 | | 3/2010 | |
| WO | WO-2010025338 | A1 * | 3/2010 | A61B 34/20 |
| WO | 2010068783 | | 6/2010 | |

* cited by examiner

ROBOTIC CATHETER SYSTEM INCLUDING IMAGING SYSTEM CONTROL

CROSS-REFERENCE TO RELATED PATENT APPLICATION

This application is a continuation of U.S. application Ser. No. 16/385,398, filed Apr. 16, 2019, which is a continuation of U.S. application Ser. No. 15/094,464, filed Apr. 8, 2016, which is a continuation of U.S. application Ser. No. 13/833,874, filed Mar. 15, 2013, which is a continuation-in-part to Application No. PCT/US12/30068, filed Mar. 22, 2012, which claims the benefit of U.S. Provisional Application No. 61/466,399, filed Mar. 22, 2011, entitled ROBOTIC CATHETER SYSTEM INCLUDING IMAGING SYSTEM CONTROL, all of which are incorporated herein by reference in their entireties.

BACKGROUND OF THE INVENTION

The present invention relates generally to the field of catheter systems for performing diagnostic and/or intervention procedures. The present invention relates specifically to catheter systems and methods incorporating control of a medical imaging system.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than standard surgery. If a patient shows symptoms indicative of cardiovascular disease, an image of the patient's heart may be taken to aid in the diagnosis of the patient's disease and to determine an appropriate course of treatment. For certain disease types, such as atherosclerosis, the image of the patient's heart may show a lesion that is blocking one or more coronary arteries. Following the diagnostic procedure, the patient may undergo a catheter based intervention procedure. During one type of intervention procedure, a catheter is inserted into the patient's femoral artery and moved through the patient's arterial system until the catheter reaches the site of the lesion. In some procedures, the catheter is equipped with a balloon or a stent that when deployed at the site of a lesion allows for increased blood flow through the portion of the coronary artery that is affected by the lesion. During certain procedures, an image of the patient's heart or vasculature is captured during the procedure to aid in the positioning of the catheter in to appropriate position for treatment. In addition to cardiovascular disease, other diseases (e.g., hypertension, etc.) may be treated using catheterization procedures.

SUMMARY OF THE INVENTION

In accordance with an embodiment, a robotic catheter procedure system configured to be operated in conjunction with a medical imaging system includes a bedside system comprising an actuating mechanism configured to engage and to impart movement to a percutaneous device and a workstation that includes a user interface configured to receive a first input and a second input, the first input indicating an upcoming percutaneous device movement and the second input received from a user, a sensor configured to detect the presence of the user's hand adjacent the user interface, wherein the first input is generated by the sensor, and a control system coupled to the user interface, the bedside system and the medical imaging system, the control system responsive to the first input and the second input and programmed to generate a first control signal based on the first input and transmit the first control signal to the medical imaging system, wherein the first control signal causes the medical imaging system to capture at least one image, and generate a second control signal based on the second input and transmit the second control signal to the bedside system, wherein the actuating mechanism causes movement of the percutaneous device in response to the second control signal, wherein the control system generates the second control signal following generation of the first control signal.

In accordance with another embodiment, a method for operating a robotic catheter procedure system and a medical imaging system includes providing a percutaneous device, providing an actuating mechanism configured to engage and to impart movement to the percutaneous device, receiving a first input indicative of upcoming percutaneous device movement, wherein the first input is received from a sensor configured to detect the presence of the user's hand adjacent a user interface, triggering capture of images by the medical imaging system in response to the first input, receiving a second input wherein the second input is received from a control, and moving the percutaneous device with the actuating mechanism in response to the second input, wherein moving the percutaneous device occurs after triggering the capture of images Alternative exemplary embodiments relate to other features and combinations of features as may be generally recited in the claims.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION OF THE PREFERRED EMBODIMENTS

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
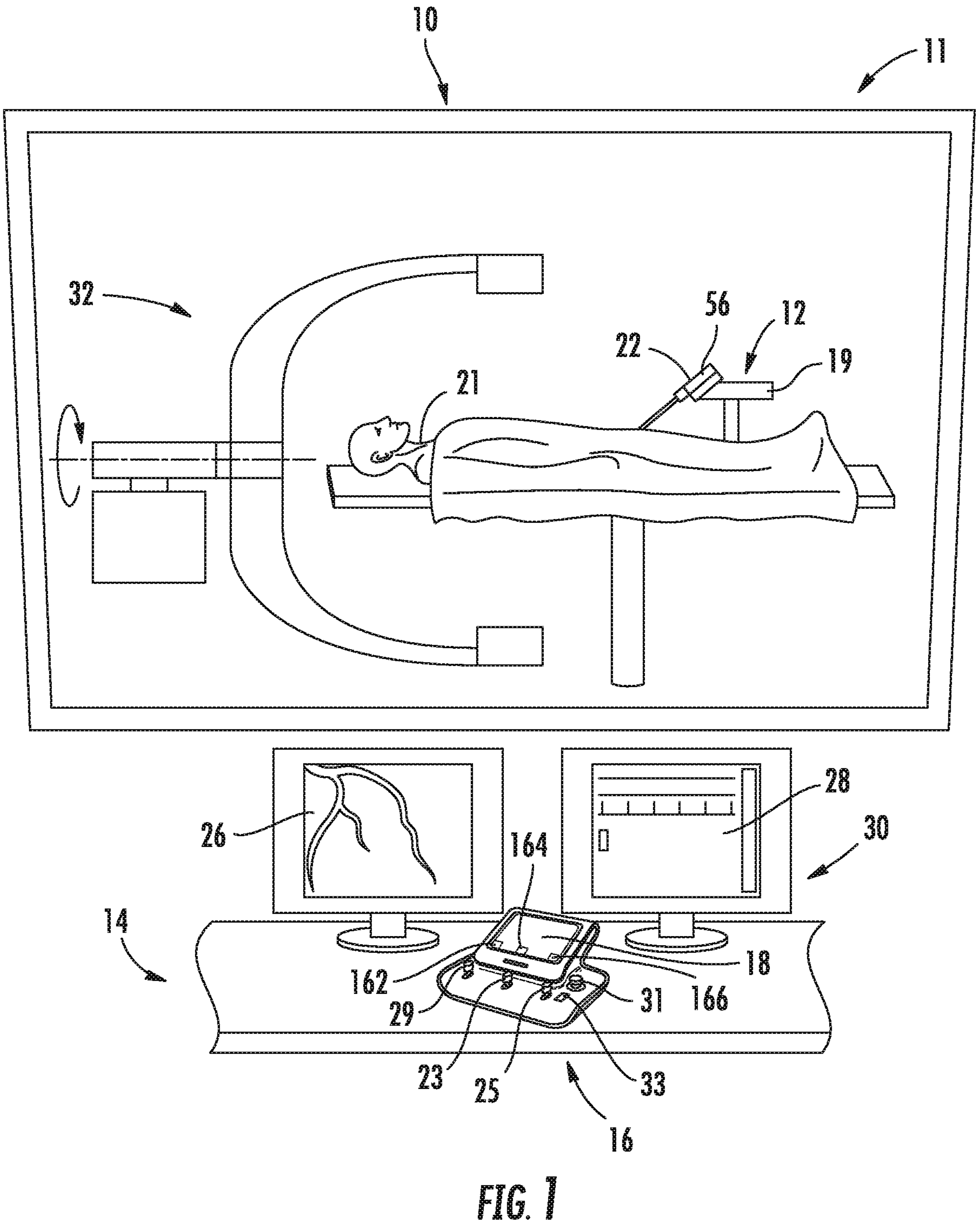
FIG. 1 is a perspective view of a catheter procedure system according to an exemplary embodiment.

Referring to FIG. 1, a catheter procedure system 10 is shown. Catheter procedure system 10 may be used to perform catheter based medical procedures (e.g., percutaneous intervention procedures). Percutaneous intervention procedures may include diagnostic catheterization procedures during which one or more catheters are used to aid in the diagnosis of a patient's disease. For example, during one embodiment of a catheter based diagnostic procedure, a contrast media is injected into one or more coronary arteries through a catheter and an image of the patient's heart is taken. Percutaneous intervention procedures may also include catheter based therapeutic procedures (e.g., balloon angioplasty, stent placement, treatment of peripheral vascular disease, etc.) during which a catheter is used to treat a disease. It should be noted, however, that one skilled in the art would recognize that certain specific percutaneous intervention devices or components (e.g., type of guide wire, type of catheter, etc.) will be selected based on the type of procedure that is to be preformed. Catheter procedure system 10 is capable of performing any number of catheter based medical procedures with minor adjustments to accommodate the specific percutaneous devices to be used in the procedure. In particular, while the embodiments of catheter procedure system 10 described herein are explained primarily in relation to the diagnosis and/or treatment of coronary disease, catheter procedure system 10 may be used to diagnose and/or treat any type of disease or condition amenable to diagnosis and/or treatment via a catheter based procedure.

Catheter procedure system 10 includes lab unit 11 and workstation 14. Catheter procedure system 10 includes a robotic catheter system, such as bedside system 12, located within lab unit 11 adjacent patient 21. Generally, bedside system 12 may be equipped with the appropriate percutaneous devices (e.g., guide wires, guide catheters, working catheters, catheter balloons, stents, diagnostic catheters, etc.) or other components (e.g., contrast media, medicine, etc.) to allow the user to perform a catheter based medical procedure. A robotic catheter system, such as bedside system 12, may be any system configured to allow a user to perform a catheter based medical procedure via a robotic system by operating various controls such as the controls located at workstation 14. Bedside system 12 may include any number and/or combination of components to provide bedside system 12 with the functionality described herein. Bedside system 12 may include a cassette 56 coupled to a base 19, and cassette 56 may include a housing 22 that supports the various components of the cassette. Various embodiments of bedside system 12 and cassette 56 are described in detail in P.C.T. International Application No. PCT/US2009/042720, filed May 4, 2009, which is incorporated herein by reference in its entirety.

In one embodiment, bedside system 12 may be equipped to perform a catheter based diagnostic procedure. In this embodiment, bedside system 12 may be equipped with one or more of a variety of catheters for the delivery of contrast media to the coronary arteries. In one embodiment, bedside system 12 may be equipped with a first catheter shaped to deliver contrast media to the coronary arteries on the left side of the heart, a second catheter shaped to deliver contrast media to the coronary arteries on the right side of the heart, and a third catheter shaped to deliver contrast media into the chambers of the heart.

In another embodiment, bedside system 12 may be equipped to perform a catheter based therapeutic procedure. In various embodiments, catheter procedure system 10 may be equipped with a guide catheter, a guide wire, and a working catheter (e.g., a balloon catheter, a stent delivery catheter, an ablation catheter, etc.). During certain therapeutic procedures an expandable percutaneous device (e.g., an angioplasty balloon, stent, etc.) may be positioned near one end of the working catheter. The working catheter is navigated through a patient's vascular system to position the expandable percutaneous device at a portion of a blood vessel that has been narrowed due to a lesion caused by a disease, such as atherosclerosis. The expandable percutaneous device is expanded at the narrowed portion to increase the diameter of the blood vessel lumen at the lesion. This expansion allows for increased blood flow through that portion of the blood vessel. In the case of balloon angioplasty, the expandable device is an angioplasty balloon that is expanded by being inflated to compress the material of the lesion which increases the diameter of the blood vessel. In the case of stent placement, a stent is expanded and left inside the blood vessel at the site of a lesion to increase the diameter of the blood vessel. In one stent placement technique, a balloon (e.g., a balloon configured to deploy a stent) is positioned in the middle of the stent, and the expansion of the balloon expands the stent.

Bedside system 12 may be equipped with a variety of catheter types as needed for a particular procedure or based on the preference of the doctor performing the procedure. In one embodiment, bedside system 12 may be equipped with a working catheter that includes a secondary lumen that is threaded over the guide wire during a procedure. In another embodiment, bedside system 12 may be equipped with an over-the-wire working catheter that includes a central lumen that is threaded over the guide wire during a procedure. In another embodiment, bedside system 12 may be equipped with an intravascular ultrasound (IVUS) catheter. In another embodiment, any of the percutaneous devices of bedside system 12 may be equipped with positional sensors that indicate the position of the component within the body.

Bedside system 12 is in communication with workstation 14, allowing signals generated by the user inputs and control system of workstation 14 to be transmitted to the various devices/systems located within lab unit 11 (e.g., bedside system 12, imaging system 32, contrast injection system 13, etc.) to control the operation of the various devices/systems. Bedside system 12 and/or imaging system 32 also may provide feedback signals (e.g., operating conditions, warning signals, error codes, etc.) to workstation 14. Bedside system 12 may be connected to workstation 14 via a communication link 38 that may be a wireless connection, cable connectors, or any other means capable of allowing communication to occur between workstation 14 and beside system 12.

Workstation 14 includes a user interface 30 configured to receive user inputs to operate various components or systems of catheter procedure system 10. User interface 30 includes controls 16. Controls 16 allow the user to control bedside system 12 to perform a catheter based medical procedure. For example, controls 16 may be configured to cause bedside system 12 to perform various tasks using the various percutaneous devices with which bedside system 12 may be equipped (e.g., to advance, retract, or rotate a guide wire, advance, retract, or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure, etc.). In some embodiments, one or more of the percutaneous intervention devices may be steerable, and controls 16 may be configured to allow a user to steer one or more steerable percutaneous device. In one such embodiment, bedside system 12 may be equipped with a steerable guide catheter, and controls 16 may also be configured to allow the user located at remote workstation 14 to control the bending of the distal tip of a steerable guide catheter. In addition, controls 16 may be configured to allow a user located at workstation 14 to control operation of imaging system 32.

In one embodiment, controls 16 include a touch screen 18, a dedicated guide catheter control 29, a dedicated guide wire control 23, and a dedicated working catheter control 25. In this embodiment, guide wire control 23 is a joystick configured to advance, retract, or rotate a guide wire, working catheter control 25 is a joystick configured to advance, retract, or rotate a working catheter, and guide catheter control 29 is a joystick configured to advance, retract, or rotate a guide catheter. In addition, touch screen 18 may display one or more icons (such as icons 162, 164, and 166) that control movement of one or more percutaneous devices via bedside system 12. Controls 16 may also include a balloon or stent control that is configured to inflate or deflate a balloon and/or a stent. Each of the controls may include one or more buttons, joysticks, touch screens, etc., that may be desirable to control the particular component to which the control is dedicated.

Controls 16 may include an emergency stop button 31 and a multiplier button 33. When emergency stop button 31 is pushed a relay is triggered to cut the power supply to bedside system 12. Multiplier button 33 acts to increase or decrease the speed at which the associated component is moved in response to a manipulation of guide catheter control 29, guide wire control 23, and working catheter control 25. For example, if operation of guide wire control 23 advances the guide wire at a rate of 1 mm/sec, pushing multiplier button 33 may cause the operation of guide wire control 23 to advance the guide wire at a rate of 2 mm/sec. Multiplier button 33 may be a toggle allowing the multiplier effect to be toggled on and off. In another embodiment, multiplier button 33 must be held down by the user to increase the speed of a component during operation of controls 16.

User interface 30 may include a first monitor 26 and a second monitor 28. First monitor 26 and second monitor 28 may be configured to display information or patient-specific data to the user located at workstation 14. For example, first monitor 26 and second monitor 28 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In one embodiment, monitors 26 and/or 28 may be configured to display an image of a portion of the patient (e.g., the patient's heart) at one or more magnification levels. In addition, first monitor 26 and second monitor 28 may be configured to display procedure specific information (e.g., duration of procedure, catheter or guide wire position, volume of medicine or contrast agent delivered, etc.). Monitor 26 and monitor 28 may be configured to display information regarding the position and/or bend of the distal tip of a steerable guide catheter. Further, monitor 26 and monitor 28 may be configured to display information to provide the functionalities associated with the various modules of controller 40 discussed below. In another embodiment, user interface 30 includes a single screen of sufficient size to display one or more of the display components and/or touch screen components discussed herein.

Catheter procedure system 10 also includes an imaging system 32 located within lab unit 11. Imaging system 32 may be any medical imaging system that may be used in conjunction with a catheter based medical procedure (e.g., angiogram system, non-digital x-ray, digital x-ray, CT, MRI, ultrasound, etc.). In an exemplary embodiment, imaging system 32 is a digital x-ray imaging device that is in communication with workstation 14. Referring to FIG. 1, imaging system 32 may include a C-arm that allows imaging system 32 to partially or completely rotate around patient 21 in order to obtain images at different angular positions relative to patient 21 (e.g., sagital views, caudal views, cranio-caudal views, etc.).

Imaging system 32 is configured to take x-ray images of the appropriate area of patient 21 during a particular procedure. For example, imaging system 32 may be configured to take one or more x-ray images of the heart to diagnose a heart condition. Imaging system 32 may also be configured to take one or more x-ray images during a catheter based medical procedure (e.g., real-time images) to assist the user of workstation 14 to properly position a guide wire, guide catheter, working catheter, stent, etc. during the procedure. The image or images may be displayed on first monitor 26 and/or second monitor 28.

Figure 2:
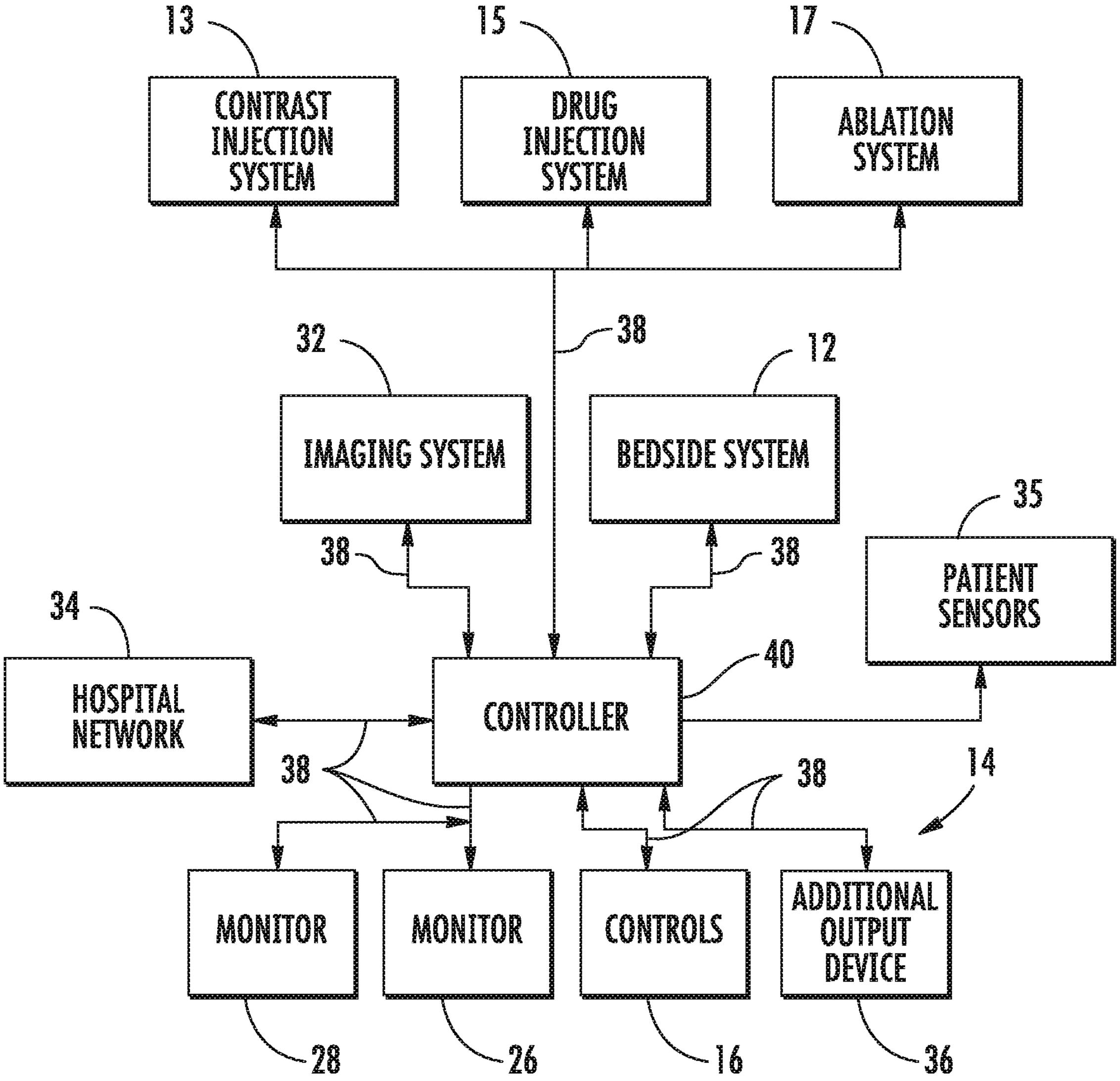
FIG. 2 is a block diagram of a catheter procedure system according to an exemplary embodiment.

Referring to FIG. 2, a block diagram of catheter procedure system 10 is shown according to an exemplary embodiment. Catheter procedure system 10 may include a control system, such as controller 40. Controller 40 may be part of workstation 14. Controller 40 is in communication with one or more bedside systems 12, controls 16, monitors 26 and 28, imaging system 32, and patient sensors 35 (e.g., electrocardiogram ("ECG") devices, electroencephalogram ("EEG") devices, blood pressure monitors, temperature monitors, heart rate monitors, respiratory monitors, etc.). In addition, controller 40 may be in communication with a hospital data management system or hospital network 34, one or more additional output devices 36 (e.g., printer, disk drive, cd/dvd writer, etc.), and a hospital inventory management system 37. Controller 40 may also be in communication with a contrast injection system 13, a drug injection system 15 and an ablation system 17.

Communication between the various components of catheter procedure system 10 may be accomplished via communication links 38. Communication links 38 may be dedicated wires or wireless connections. Communication links 38 may also represent communication over a network. Catheter procedure system 10 may be connected or configured to include any other systems and/or devices not explicitly shown. For example, catheter procedure system 10 may include IVUS systems, image processing engines, data storage and archive systems, automatic balloon and/or stent inflation systems, medicine tracking and/or logging systems, user logs, encryption systems, systems to restrict access or use of catheter procedure system 10, robotic catheter systems of the past, present, or future, etc.

Figure 3:
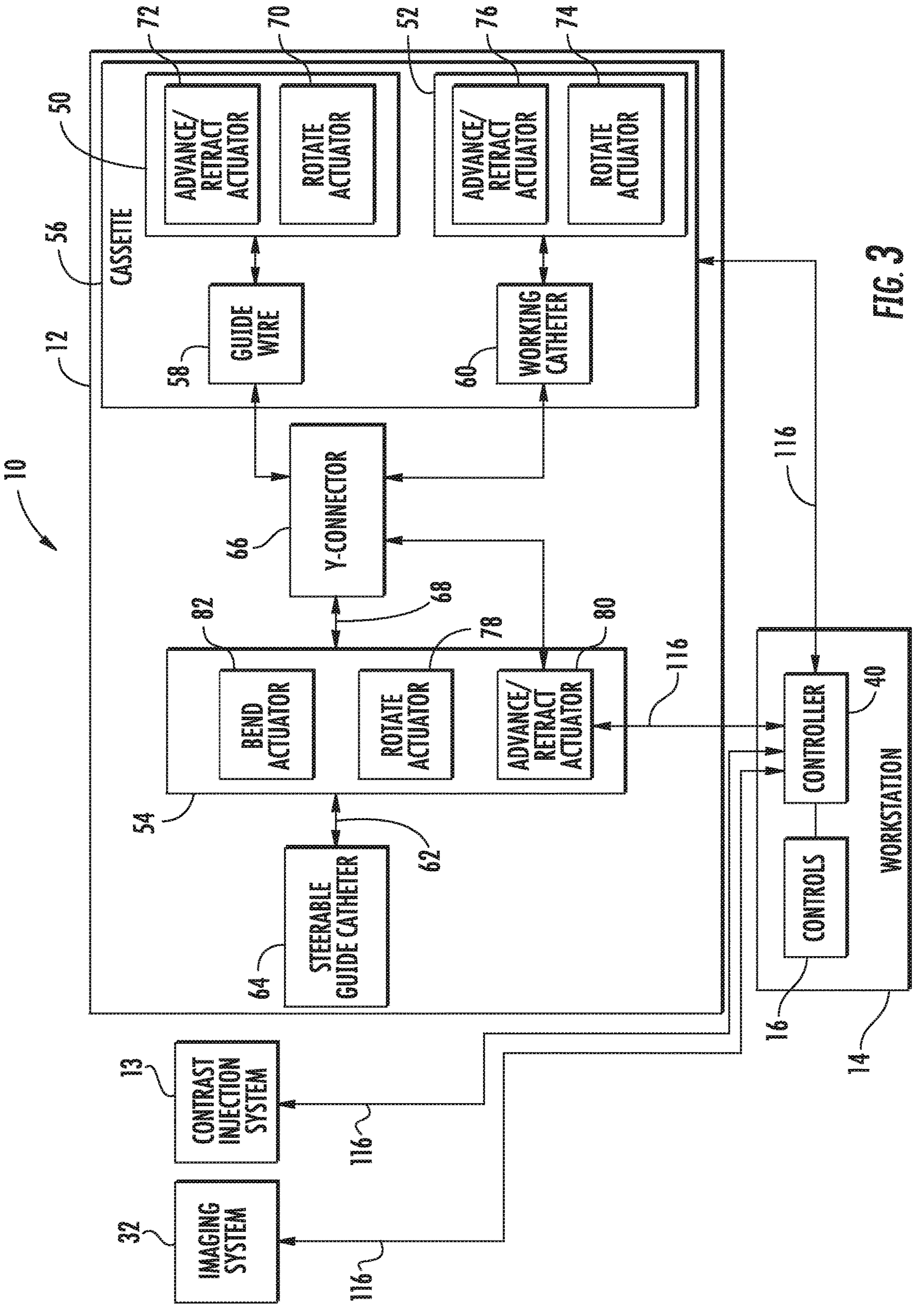
FIG. 3 is a block diagram of a catheter procedure system depicting a bedside system, an imaging system and a contrast injection system according to an exemplary embodiment.

Referring to FIG. 3, a block diagram of catheter procedure system 10 is shown according to an exemplary embodiment. Catheter procedure system 10 may include various actuating mechanisms that engage and impart motion to an associated percutaneous device in response to a user's manipulation of controls 16 and/or under control of controller 40. In one embodiment, catheter procedure system 10 includes a guide wire actuating mechanism 50, a working catheter actuating mechanism 52, and a guide catheter actuating mechanism 54. In other embodiments, catheter procedure system 10 may include an actuating mechanism for inflating an angioplasty or stent delivery balloon. In one embodiment, guide wire actuating mechanism 50 and working catheter actuating mechanism 52 are incorporated within cassette 56. Additional embodiments of bedside system 12 and cassette 56 are described in detail in P.C.T. International Application No. PCT/US2009/042720, filed May 4, 2009, which is incorporated herein by reference in its entirety.

Guide wire actuating mechanism 50 is coupled to guide wire 58 such that guide wire actuating mechanism 50 is able to cause guide wire 58 to advance, retract, and rotate. Working catheter actuating mechanism 52 is coupled to working catheter 60 such that working catheter actuating mechanism 52 is able to cause working catheter 60 to advance, retract, and rotate. Connector 62 couples guide catheter 64 to guide catheter actuating mechanism 54 such that guide catheter actuating mechanism 54 is able to cause guide catheter 64 to advance, retract, and rotate. In various embodiments, guide wire actuating mechanism 50, working catheter actuating mechanism 52, and guide catheter actuating mechanism 54 may each include an engagement structure suitable for engaging the respective percutaneous device such that the actuating mechanism is able to impart axial and/or rotational movement to the percutaneous device.

A Y-connector 66 is coupled to guide catheter actuating mechanism 54 via connector 68. In various embodiments, connector 68 may be a component separate from both Y-connector 66 and guide catheter actuating mechanism 54. In other embodiments, connector 68 may be part of (e.g., integral with) Y-connector 66 or part of actuating mechanism 54. In one embodiment, Y-connector 66 is also connected to cassette 56.

In one embodiment, Y-connector 66 includes a first leg, a second leg, and a third leg. The first leg of the Y-connector is connected to or in communication with the internal lumen of guide catheter 64. The second leg is angled away from the longitudinal axis of guide catheter 64. The second leg provides a port for the injection of fluids (e.g., contrast media, medicine, etc.) into the lumen of guide catheter 64. As shown in FIG. 3, contrast injection system 13 is coupled to the second leg of Y-connector 66 via a conduit 65 that allows contrast media to be delivered from contrast injection system 13 to Y-connector 66. The third leg of Y-connector 66 is coupled to a cassette 56 and receives both guide wire 58 and working catheter 60. Thus, by this arrangement, guide wire 58 and working catheter 60 are inserted through Y-connector 66 into the internal lumen of guide catheter 64.

Guide wire actuating mechanism 50 includes a rotate actuator 70 and an advance/retract actuator 72. Rotate actuator 70 is configured to cause rotation of guide wire 58 about its longitudinal axis. Advance/retract actuator 72 is configured to advance and/or retract guide wire 58 (i.e., to advance and/or retract along the longitudinal axis of the guide wire) within patient 21. Working catheter actuating mechanism 52 includes a rotate actuator 74 and an advance/retract actuator 76. Rotate actuator 74 is configured to cause rotation of working catheter 60 about its longitudinal axis. Advance/retract actuator 76 is configured to advance and/or retract working catheter 60 (i.e., to advance and/or retract along the longitudinal axis of the working catheter) within patient 21.

Guide catheter actuating mechanism 54 includes a rotate actuator 78, an advance/retract actuator 80, and a bend actuator 82. Rotate actuator 78 is configured to cause rotation of guide catheter 64 about its longitudinal axis. Advance/retract actuator 80 is configured to advance and/or retract guide catheter 64 (i.e., to advance and/or retract along the longitudinal axis of the guide catheter) within patient 21. In some embodiments, guide catheter 64 may include one or more bend control elements that allow the user to cause bending of the distal tip of guide catheter 64. In such an embodiment, bend actuator 82 causes the distal tip of guide catheter 64 to bend in response to the user's manipulation of controls 16.

Referring to the block diagram of FIG. 3, controls 16 and controller 40 located at workstation 14 are communicably coupled to various portions of bedside system 12 to allow the user to control movement of guide wire 58, working catheter 60 and guide catheter 64 and any other percutaneous devices that bedside system 12 is equipped with. Controls 16 and controller 40 are communicably coupled to guide catheter actuating mechanism 54 to allow the user to move guide catheter 64. In addition, controls 16 are communicably coupled to cassette 56 to allow the user to control guide wire 58 via guide wire actuating mechanism 50 and to control working catheter 60 via working catheter actuating mechanism 52. In various embodiments, controller 40 may be configured to provide automated movement of a percutaneous device.

In one embodiment, cassette 56 is configured to be coupled to a motor drive base 19 (shown in FIG. 1). In this embodiment, each of the actuators 70, 72, 74, and 76 of cassette 56 are configured to engage capstans extending from the motor drive base. Motors located within the motor drive base drive (e.g., rotate) the capstans, which in turn drive the actuators 70, 72, 74, and 76 of cassette 56. When the actuators 70, 72, 74, and 76 of cassette 56 are engaged with guide wire 58 and working catheter 60, respectively, the actuators 70, 72, 74, and 76 of cassette 56 transfer the rotational movement of the capstans to cause the movement of guide wire 58 and working catheter 60. In another embodiment, the motors that drive the capstans of the motor drive base may be located outside of the base connected to cassette 56 via an appropriate transmission device (e.g., shaft, cable, etc.). In yet another embodiment, cassette 56 includes motors located within cassette 56 associated with the actuators 70, 72, 74, and 76, and cassette 56 is mounted to a base providing a power supply (e.g., battery, AC building power supply, etc.) to the motors within cassette 56.

Catheter procedure system 10 is also configured to provide control of imaging system 32 and contrast injection system 13 via controls 16 and/or controller 40. As shown in FIG. 3, controls 16 and controller 40 are located at workstation 14 and are communicably coupled to imaging system 32 and to contrast injection system 13 to allow the user to control imaging system 32 and contrast injection system 13 from workstation 14. As explained in more detail below, catheter procedure system 10 is configured such that control of imaging system 32 and/or contrast injection system 13 is integrated with control of bedside system 12 to provide for convenient, efficient and intuitive control over both systems by a user located at workstation 14. In various embodiments, various functions of imaging system 32 (e.g., image capture, magnification, collimation, c-arm positioning, etc.) may be controlled via controls 16 and/or controller 40. For example, controls 16 may be configured to allow the user positioned at workstation 14 to directly control operation of imaging system 32 via interaction with controls 16 that specifically operate imaging system 32 (e.g., via interaction with an imaging start button, an image system "on-off" button, an image system touch screen icon, a user entered text command to start imaging, selection of an imaging activation element from a drop down menu, etc.). In addition, catheter procedure system 10 may be configured to provide for automatic, intelligent or semi-automatic control of imaging system 32 via controller 40 (e.g., without requiring the user to interact with a control specific to the imaging system).

In one embodiment, the user of workstation 14 may be able to control the angular position of imaging system 32 relative to the patient to obtain and display various views of the patient's heart on first monitor 26 and/or second monitor 28 via operation of controls 16. In another embodiment, controller 40 may automatically control the angular position of imaging system 32 according to a particular module or set of instructions. Displaying different views at different portions of the procedure may aid the user of workstation 14 to properly move and position the percutaneous devices within the 3D geometry of the patient's heart. For example, displaying the proper view during a procedure may allow the user to view a patient's vascular system from the proper angle to ensure that the distal tip of a steerable guide catheter is bent in the proper way to ensure the catheter is moved as intended. In an exemplary embodiment, imaging system 32 may be any 3D imaging modality of the past, present, or future, such as an x-ray based computed tomography (CT) imaging device, a magnetic resonance imaging device, a 3D ultrasound imaging device, etc. In this embodiment, the image of the patient's heart that is displayed during a procedure may be a 3D image.

Figure 4:
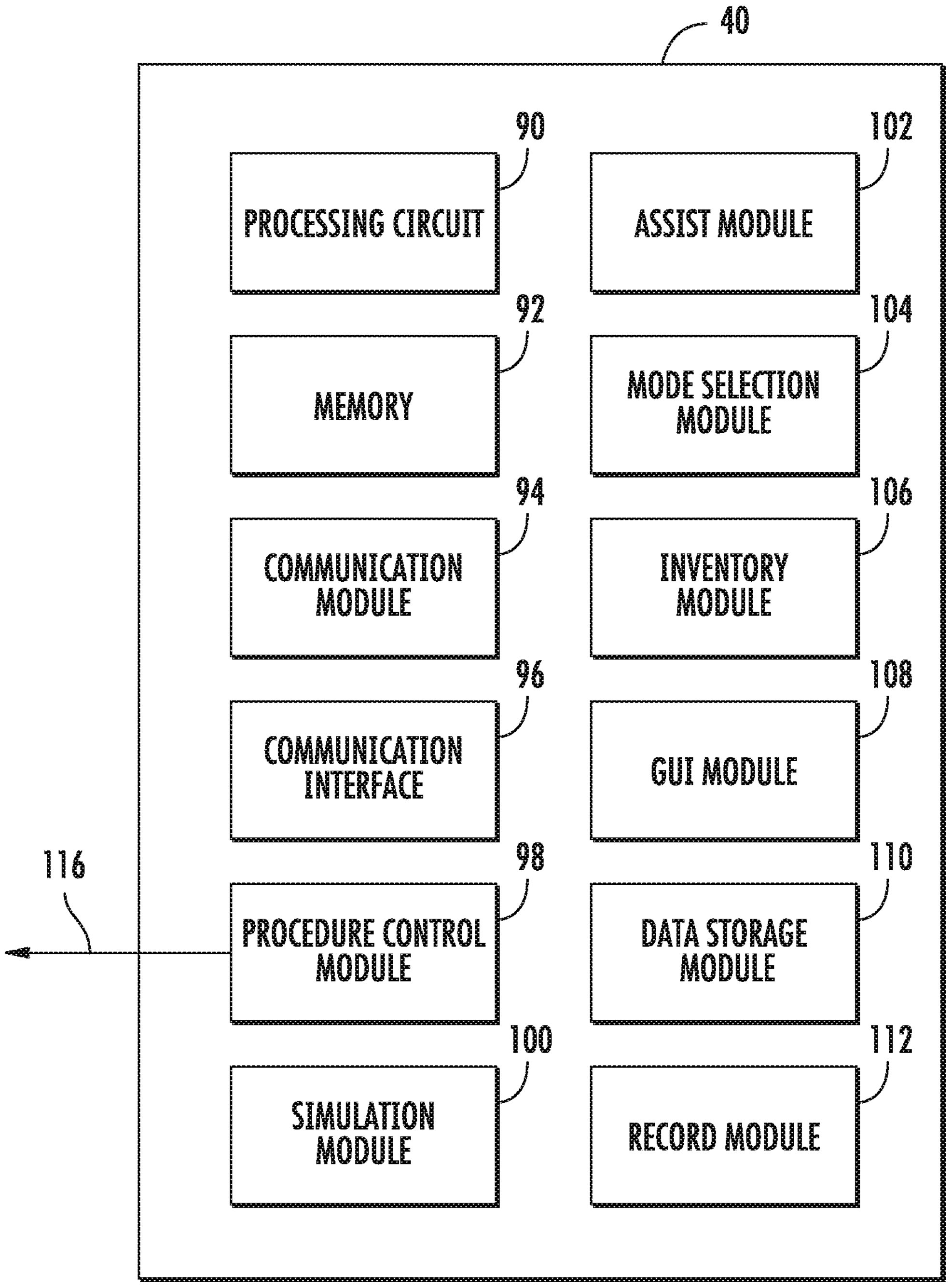
FIG. 4 is a block diagram of a controller for controlling a robotic catheter system according to an exemplary embodiment.

Referring to FIG. 4, a block diagram of a control system, such as controller 40, is shown according to an exemplary embodiment. Controller 40 generally may be an electronic control unit suitable to provide catheter procedure system 10 with the various functionalities described herein. For example, controller 40 may be an embedded system, a dedicated circuit, a general purpose system programmed with the functionality described herein, etc. Controller 40 includes a processing circuit 90, memory 92, communication module or subsystem 94, communication interface 96, procedure control module or subsystem 98, simulation module or subsystem 100, assist control module or subsystem 102, mode selection module or subsystem 104, inventory module or subsystem 106, GUI module or subsystem 108, data storage module or subsystem 110, and record module or subsystem 112. In one embodiment, controller 40 may include a movement instruction module that includes one or more instruction sets that dictate how bedside system 12 responds to a user's manipulation of controls 16 to cause a percutaneous device to move in a particular way. The movement instruction module may include various instruction sets to facilitate traversal of a vascular occlusion by the percutaneous devices as discussed herein. Various embodiments of a catheter procedure system 10 including a movement instruction module are disclosed in P.C.T. International Application No. PCT/US2010/52178, filed Oct. 11, 2010, which is incorporated herein by reference in its entirety.

Processing circuit 90 may be a general purpose processor, an application specific processor (ASIC), a circuit containing one or more processing components, a group of distributed processing components, a group of distributed computers configured for processing, etc., configured provide the functionality of module or subsystem components 94, 98-112. Memory 92 (e.g., memory unit, memory device, storage device, etc.) may be one or more devices for storing data and/or computer code for completing and/or facilitating the various processes described in the present disclosure. Memory 92 may include volatile memory and/or non-volatile memory. Memory 92 may include database components, object code components, script components, and/or any other type of information structure for supporting the various activities described in the present disclosure.

According to an exemplary embodiment, any distributed and/or local memory device of the past, present, or future may be utilized with the systems and methods of this disclosure. According to an exemplary embodiment, memory 92 is communicably connected to processing circuit 90 and module components 94, 98-112 (e.g., via a circuit or any other wired, wireless, or network connection) and includes computer code for executing one or more processes described herein. A single memory unit may include a variety of individual memory devices, chips, disks, and/or other storage structures or systems.

Module or subsystem components 94, 98-112 may be computer code (e.g., object code, program code, compiled code, script code, executable code, non-transitory programmed instructions, or any combination thereof), hardware, software, or any combination thereof, for conducting each module's respective functions. Module components 94, 98-112 may be stored in memory 92, or in one or more local, distributed, and/or remote memory units configured to be in communication with processing circuit 90 or another suitable processing system.

Communication interface 96 includes one or more component for communicably coupling controller 40 to the other components of catheter procedure system 10 via communication links 38. Communication interface 96 may include one or more jacks or other hardware for physically coupling communication links 38 to controller 40, an analog to digital converter, a digital to analog converter, signal processing circuitry, and/or other suitable components. Communication interface 96 may include hardware configured to connect controller 40 with the other components of catheter procedure system 10 via wireless connections. Communication module 94 is configured to support the communication activities of controller 40 (e.g., negotiating connections, communication via standard or proprietary protocols, etc.).

Data storage module 110 is configured to support the storage and retrieval of information by controller 40. In one embodiment, data storage module 110 is a database for storing patient specific data, including image data. In another embodiment, data storage module 110 may be located on hospital network 34. Data storage module 110 and/or communication module 94 may also be configured to import and/or export patient specific data from hospital network 34 for use by controller 40. Controller 40 includes a GUI module 108 the controls the display of various information on the display devices (e.g., monitors 26 and 28, touch screen 18, etc.) of workstation 14. In one embodiment, GUI module 108 is configured to display image data captured by imaging system 32 during a procedure to assist the user of catheter procedure system 10 perform a procedure.

Controller 40 also includes a procedure control module 98 configured to support the control of various devices/systems located within lab unit 11 (e.g., bedside system 12, imaging system 32, contrast injection system 13, etc.) by a user located at workstation 14 during a catheter based medical procedure. In various embodiments, procedure control module 98 allows the user to operate bedside system 12, imaging system 32, and/or contrast injection system 13 by manipulating controls 16. In such embodiments, procedure control module 98 is configured to generate one or more control signals 116 based upon the user's manipulation of controls 16 and/or based upon other data, modules, instruction sets, etc. available to procedure control module 98. Control signals 116 may also be generated by controller 40 to provide for automatic (e.g., control signals not based on user operation of controls 16) or semi-automatic (e.g., control signals partially based on user operation of controls 16) control of bedside system 12, imaging system 32, contrast injection system 13, etc.

Referring back to FIG. 3, control signals 116 generated by procedure control module 98 are communicated from controller 40 to the various actuators of bedside system 12, to imaging system 32, to contrast injection system 13, and to any other device or system controlled by controller 40. Referring to bedside system 12, in response to control signals 116, the actuators of cassette 56 cause movement of the guide wire, working catheter and/or guide catheter. Thus, in this manner, the actuators of bedside system 12 cause movement of the percutaneous devices in response to user inputs received by controls 16 and based on other data or control schemes discussed herein. In addition, various functions of imaging system 32 (e.g., image capture, magnification, collimation, c-arm positioning, etc.) are controlled in response to control signals 116, and injection of contrast media into the patient by contrast injection system 13 is controlled in response to control signals 116.

Procedure control module 98 may also cause data appropriate for a particular procedure to be displayed on monitors 26 and 28. Procedure control module 98 may also cause various icons (e.g., icons 162, 164, 166, etc.) to be displayed on touch screen 18 that the user may interact with to control the use of bedside system 12.

Figure 5:
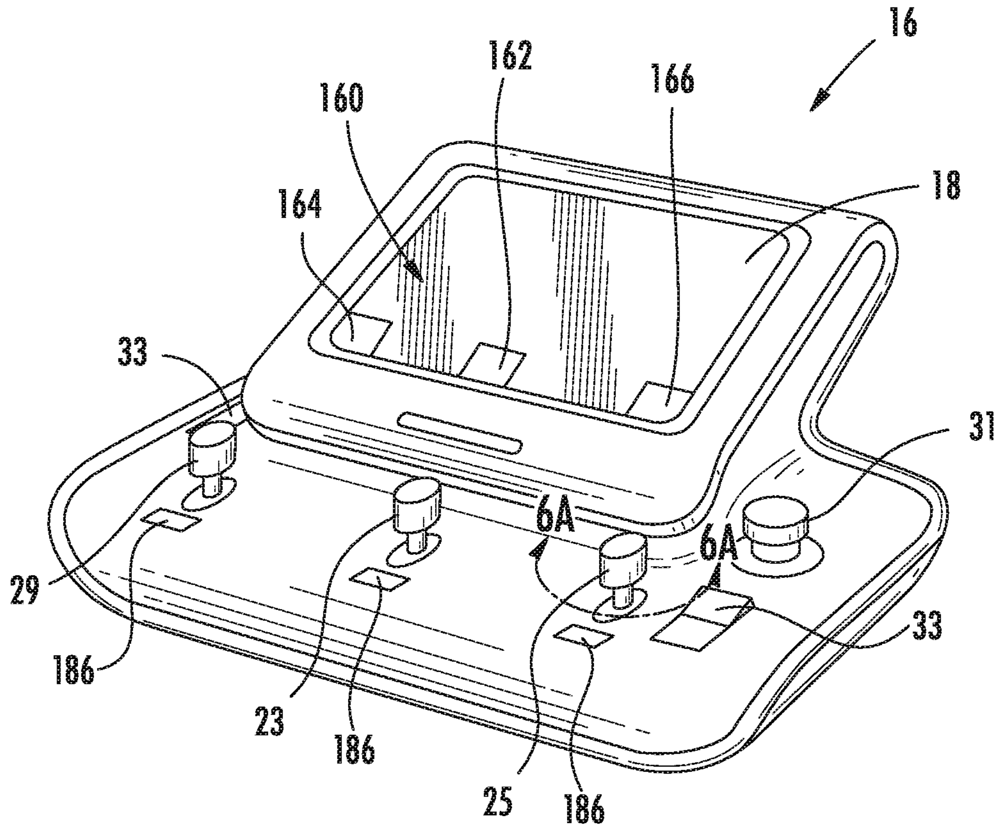
FIG. 5 is a perspective view of controls for a robotic catheter system according to an exemplary embodiment.

Referring to FIG. 5, an enlarged view of controls 16 are shown according to an exemplary embodiment. As shown in FIG. 5, controls 23, 25 and 29 are joystick controls that, when actuated by the user, cause procedure control module 98 to generate one or more control signals 116 which in turn cause bedside system 12 to move (e.g., advance, retract, rotate, etc.) the guide wire, working catheter and guide catheter, respectively. In this embodiment, the movement rate of a percutaneous device caused by bedside system 12 is a function of or is proportional to the degree of displacement of the joystick from the resting position and the direction of movement is a function of the direction of joystick displacement.

As noted above, catheter procedure system 10 may be configured such that control of imaging system 32 and contrast injection system 13 are integrated with control of bedside system 12 to provide for convenient, efficient and intuitive control over both systems by a user located at workstation 14. In particular, catheter procedure system 10 may be configured to automatically activate image capture by imaging system 32 immediately prior to percutaneous device movement, to maintain image capture during percutaneous device movement and to automatically cease image capture following percutaneous device movement.

Figure 6:
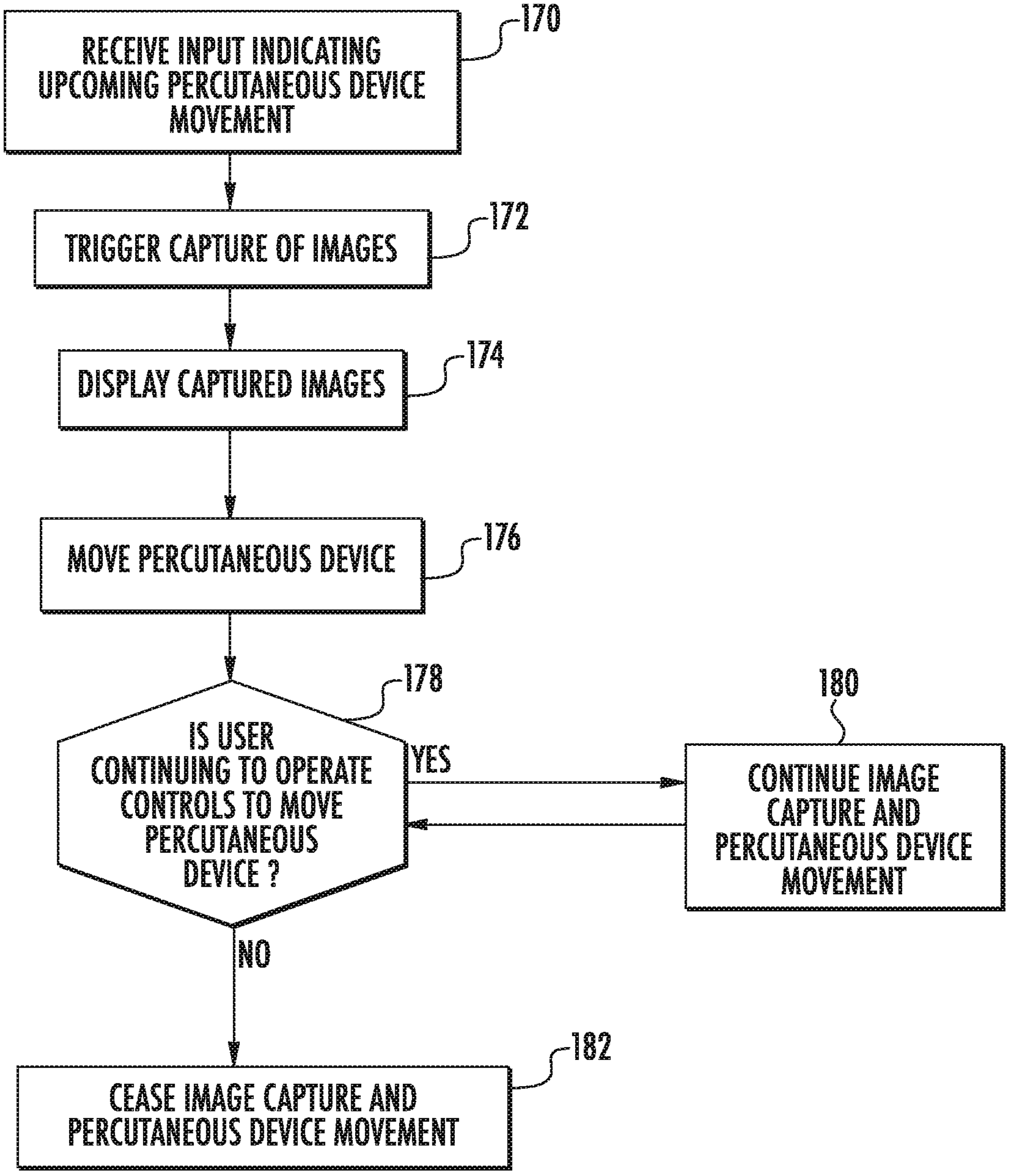
FIG. 6 is a flow diagram showing control of an imaging system and a percutaneous device according to an exemplary embodiment.

FIG. 6 is a flow-diagram depicting a process of automatic image capture integrated with control of a robotic catheter system according to an exemplary embodiment. The process shown in FIG. 6 may be performed by a controller 40 including a module (e.g., procedure control module 98) that is configured to provide this functionality.

At step 170, controller 40 of catheter procedure system 10 receives an input indicative of upcoming percutaneous device movement. For example, the input received at step 170 may indicate that the user located at workstation 14 intends to move a percutaneous device with bedside system 12 by interacting with controls 16. At step 172, procedure control module 98 automatically generate a control signal 116 based upon the input received at step 170. The control signal generated at step 172 are communicated to imaging system 32, and imaging system 32 is responsive to these control signals to trigger capture of images. The images captured in response to these control signals are captured prior to movement of the percutaneous device. At step 174, the captured images are displayed to the user located at workstation 14 via a display, such as monitors 26 and 28.

At step 176, procedure control module 98 generates one or more control signals 116 that are communicated to one or more actuator of bedside system 12 (in addition to the control signals causing image capture) to cause movement of the percutaneous device in accordance with the user's manipulation of controls 16. At step 178, procedure control module 98 determines whether the user is still operating controls 16 to cause movement of the percutaneous device. If the user is still operating controls 16, then at step 180 procedure control module 98 continues to generate control signals to capture images via imaging system 32, to display images on monitors 26 and 28 and to cause movement of the percutaneous device via bedside system 12. In this manner, images captured by image system 32 are displayed immediately prior to percutaneous device movement and continuously during percutaneous device movement.

If the user has stopped operating controls 16, then at step 182 both image capture and percutaneous device movement are stopped. Thus, in this embodiment, procedure control module 98 is configured to control both image capture and percutaneous device movement in an intuitive manner via user interaction with a single control associated with the percutaneous device. This eliminates the need for the user to independently and separately actuate a separate control (e.g., a dedicated imaging system activation button) to trigger image capture prior to percutaneous device movement.

In one embodiment, procedure control module 98 is configured to continuously cause the display of the last image captured by imaging system 32 on monitors 26 or 28 after device movement has stopped. In this embodiment, the user located at workstation 14 can easily view the last captured image as the user decides the next action to take during the procedure.

Figure 7A:
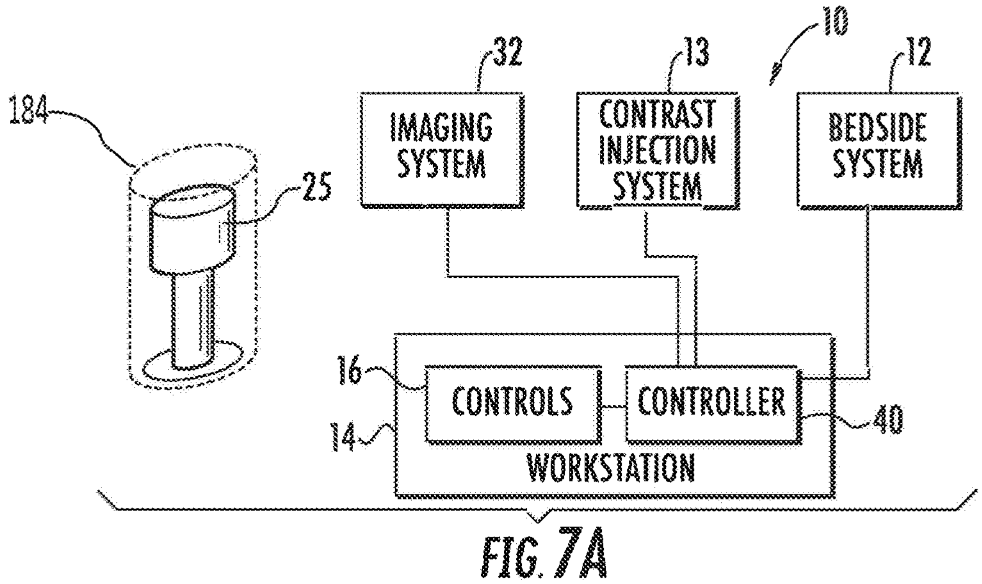
FIG. 7A is an enlarged perspective view of a control for a robotic catheter system in a resting position according to an exemplary embodiment.
Figure 7B:
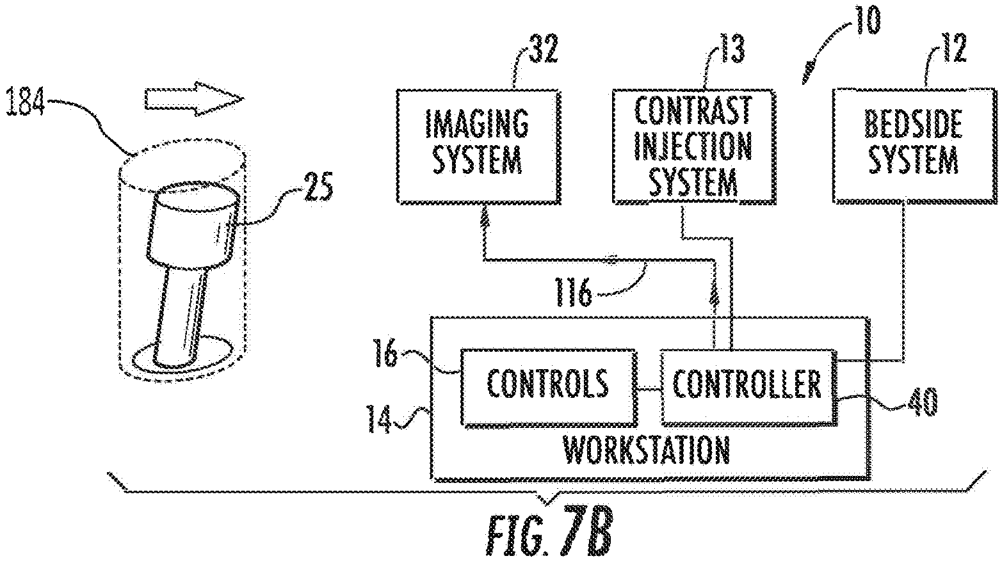
FIG. 7B is an enlarged perspective view of a control for a robotic catheter system in a first actuated position according to an exemplary embodiment.
Figure 7C:
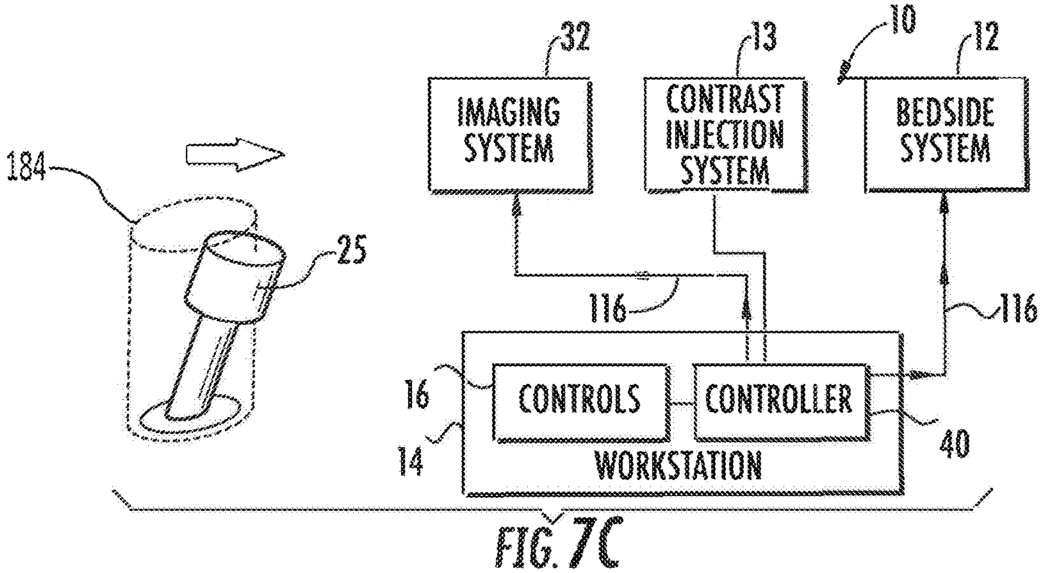
FIG. 7C is an enlarged perspective view of a control for a robotic catheter system in a second actuated position according an to exemplary embodiment.

FIGS. 7A-7C show a catheter procedure system 10 configured to receive an input indicative of upcoming percutaneous device movement. Controller 40 (e.g., via instructions of procedure control module 98) is configured such that image capture via imaging system 32 is triggered when the user first begins to interact with one of the input devices or controls of controls 16 but prior to triggering movement of the percutaneous device in response to the user's interaction with the input device.

Referring to FIG. 7A, a control, for example working catheter joystick 25, is shown in the resting position (e.g., the non-actuated position, prior to movement of the control by the user). Working catheter control 25 may include an activation zone 184 surrounding control 25 such that control 25 is located within activation zone 184 when the control is in the resting position. With the control in the resting position, controller 40 does not generate control signals to either imaging system 32 or bedside system 12.

Referring to FIG. 7B, control 25 is shown displaced from the resting position but still within activation zone 184, and in this embodiment, this position of control 25 generates the input indicative of upcoming percutaneous device movement that is received at step 170 in FIG. 6. When the control 25 has been displaced from the resting position but is still within activation zone 184 as shown in FIG. 7B, procedure control module 98 is configured to generates one or more control signals 116 to instruct imaging system 32 to begin image capture but does not generate control signals 116 to the actuators of bedside system 12. Thus, in this embodiment, activation zone 184 is the zone in which control 25 may be actuated from the resting position such that image capture is triggered but device movement is not yet started.

Referring to FIG. 7C, control 25 is shown displaced such that the control has moved outside of activation zone 184. Once control 25 has been actuated out of activation zone 184, as shown in FIG. 7C, procedure control module 98 is configured to generate a control signal 116 that is communicated to an actuator of bedside system 12 to cause movement of the percutaneous device in accordance with the movement of the control 25. In this embodiment, when control 25 is in the position shown in FIG. 7C, procedure control module 98 is configured to continue to generate the control signals that cause capture of images at the same time as it is generating the control signals that cause movement of the percutaneous device. In this manner, image capture and display continues to occur as the percutaneous device is being moved by the user. Thus, in this embodiment, the input that triggers image capture and the input that triggers movement of the percutaneous device are received from a user by a single control. Lastly, procedure control module 98 is configured to stop generation of both the control signals to imaging system 32 and to bedside system 12 when control 25 is returned to the resting position of FIG. 7A.

As discussed above regarding FIGS. 7A-7C, activation zone 184 is a graphical representation of the amount of displacement of control 25 that is necessary to generate control signals to imaging system 32 and to bedside system 12 (i.e., the size of activation zone 184). The size of activation zone 184 may be determined by the configuration of procedure control module 98. For example, procedure control module 98 may include computer code or instructions that dictate how much displacement of the control is necessary to generate the different control signals. In various embodiments, procedure control module 98 will be configured such that size of activation zone 184 is fairly small (e.g., less than 1 mm, less than 5 mm, less than 10 mm, etc.) to ensure that control 25 does not need to be moved a large distance in order to trigger movement of the percutaneous device.

The embodiment shown in FIGS. 7A-7C utilizes the amount of displacement of a percutaneous device control as the input that indicates upcoming percutaneous device movement and that automatically triggers image capture prior to percutaneous device movement. In other embodiments, other mechanisms may be used. For example, procedure control module 98 may be configured such that once working catheter control 25 is actuated by the user, image capture by imaging system 32 is triggered and movement of the percutaneous device in response to the user operation of control 25 is delayed until image acquisition and display has started. In this embodiment, the input indicative of upcoming percutaneous device movement is the input received by controller 40 that is generated by actuation of control 25. In this embodiment, the input that triggers image capture is initial interaction with control 25 by the user, and controller 40 generates the control signal to bedside system 12 to cause movement of the percutaneous device after a predetermined time following generation of the control signal to the imaging system.

In another embodiment, controller 40 may receive feedback signals from imaging system 32 or from the display components indicating that image acquisition and display has started. Once image acquisition has started and the image is displayed, procedure control module 98 then generates control signals to bedside system 12 to cause movement of the percutaneous device in accordance with the user's manipulation of the control. In one such embodiment, controller 40 may be configured to generate the control signal to bedside system 12 to cause movement of the percutaneous device only after the imaging system has begun image capture.

In other embodiments, the input indicative of the user's intent to move a percutaneous device may be generated by devices other than one of the percutaneous device controls of workstation 14. In one such embodiment, workstation 14 may include one or more sensors 186 (shown in FIG. 5) configured to detect the presence of a user's hand approaching one of the percutaneous device controls (e.g., controls 23, 25, 29) of controls 16. The sensors may be a one or more of a variety of different proximity sensors (e.g., infrared sensors, optical sensors, capacitive sensors, reflective sensors, etc.) mounted to the housing of controls 16 and adjacent to the individual input device of controls 16 that the sensor is associated with. In this embodiment, activation zone 184 is established by the proximity sensor, and upcoming percutaneous device movement is indicated by the proximity sensor when the user's hand is detected within the activation zone. The proximity sensor transmits a "presence" signal to controller 40 when the proximity sensor detects the presence of a user's hand adjacent the control, and, based upon this input from the proximity sensor, controller 40 generates one or more control signal 116 to trigger image capture by imaging system 32.

Following the start of image acquisition, movement of the percutaneous device is then triggered as the user continues to actuate the control (e.g., working catheter control 25). In one such embodiment, procedure control module 98 may be configured to stop image capture and percutaneous device movement when the control is returned to the resting position. In another embodiment, procedure control module 98 may be configured to stop percutaneous device movement when the control is returned to the resting position and to stop image acquisition when the proximity sensor indicates that the user's hand has exited activation zone 184.

In another embodiment instead of receiving an input indicative of upcoming movement from a physical input device, controller 40 may include a prediction module that is configured (e.g., programmed) with an algorithm that predicts when the next movement of a percutaneous device is likely to be initiated based on identified patterns of use of the various controls. In this embodiment, the prediction module provides the input indicative of upcoming device movement to procedure control module 98, and procedure control module 98 then triggers image capture prior to the predicted time of movement initiation. For example, if the control use pattern indicates that working catheter control 25 is typically actuated after a certain time period (e.g., 10 seconds) following operation of guide wire control 23, procedure control module 98 may be configured to trigger image capture via imaging system 32 immediately before the time period expires following operation of guide wire control 23.

In another embodiment, the input indicative of upcoming percutaneous device movement is not an input generated by a dedicated or specific imaging system control (e.g., via interaction with an imaging start button, an image system on button, an image system touch screen icon, a user entered text command to start imaging, selection of an imaging activation element from a drop down menu, etc.). In one such embodiment, controls 16 may include a dedicated or specific imaging system control to allow the user to directly control imaging system 32 independent from the automatic or semi-automatic control that is based on the input indicative of upcoming device movement.

It should be understood that while only working catheter joystick 25 is shown in FIGS. 7A-7C, any control (e.g., guide wire control 23, guide catheter control 29, touch screen icons 162, 164, 166, etc.) located at workstation 14 may include various activation zones as discussed above.

Figure 8:
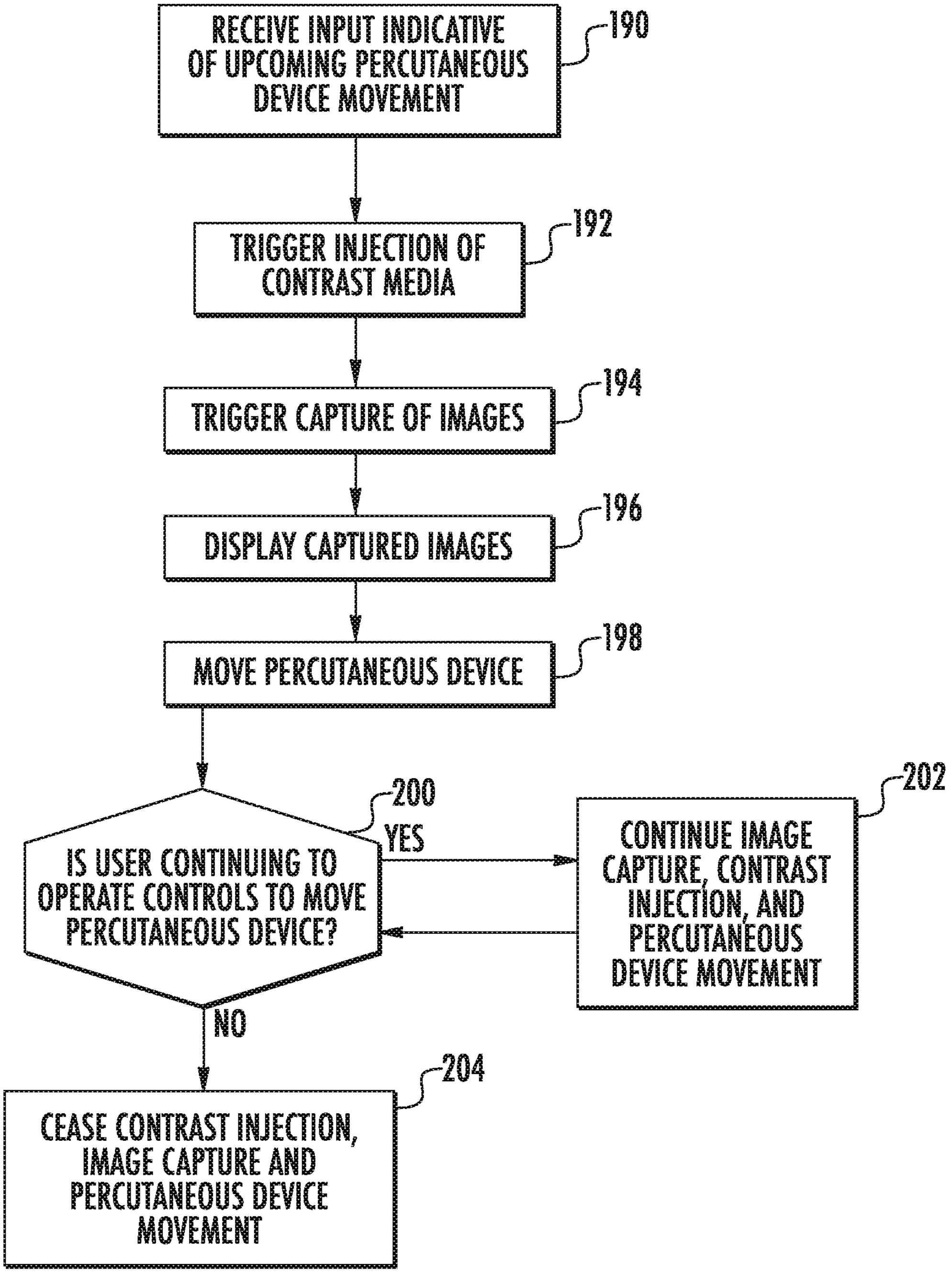
FIG. 8 is a flow diagram showing control of a contrast injection device, an imaging system and a percutaneous device according to an exemplary embodiment.

As shown in FIG. 3, controller 40 may be in communication with contrast injection system 13. Various embodiments of a catheter procedure system including a contrast media injection system are described in detail in P.C.T. International Application No. PCT/US2009/067540, filed Dec. 10, 2009, which is incorporated herein by reference in its entirety. In embodiments where catheter procedure system is equipped with a contrast injection system 13, catheter procedure system 10 may be configured to automatically trigger injection of contrast media via contrast injection system 13 prior to percutaneous device movement and prior to automatic image capture to ensure sufficient contrast media is present within a patient's vasculature during image capture. In such embodiments, controller 40 is configured to generate one or more control signal 116 to contrast injection system 13 based upon an input indicative of upcoming percutaneous device movement. FIG. 8 is a flow-diagram depicting a process of automatic contrast media injection and automatic image capture integrated with control of a robotic catheter system according to an exemplary embodiment. The process shown in FIG. 8 may be performed by a controller 40 including a module (e.g., procedure control module 98) that is configured to provide this functionality.

At step 190, catheter procedure system 10 receives an input indicating that the user located at workstation 14 intends to move a percutaneous device with bedside system 12 by interacting with controls 16. Any of the inputs indicating upcoming device movement discussed above may be received at step 190. At step 192, procedure control module 98 automatically generates control signals 116 based upon the input received at step 190, and the generated control signals 116 are communicated to contrast injection system 13 to trigger injection of contrast media prior to both image capture and movement of the percutaneous device. At step 194, procedure control module 98 automatically generates control signals 116 based upon the input received at step 190, and the generated control signals 116 are communicated to imaging system 32 to trigger image capture by imaging system 32 prior to movement of the percutaneous device but after injection of contrast media at step 192. At step 196, the captured images are displayed to the user located at workstation 14 via a display, such as monitors 26 and 28.

At step 198, procedure control module 98 generates one or more control signals 116 that are communicated to one or more actuator of bedside system 12 (in addition to the control signals causing image capture and contrast injection) to cause movement of the percutaneous device in accordance with the user's manipulation of controls 16. At step 200, procedure control module 98 determines whether the user is still operating controls 16 to cause movement of the percutaneous device. If the user is still operating controls 16, then at step 202 procedure control module 98 continues to generate control signals to periodically inject contrast media via contrast injection system 13, to capture images via imaging system 32, to display the captured images and to cause movement of the percutaneous device via bedside system 12. In this manner, images captured by image system 32 are displayed immediately prior to percutaneous device movement and continuously during percutaneous device movement.

If the user has stopped operating controls 16, then at step 204, contrast injection, image capture and percutaneous device movement are stopped when the user stops manipulating controls 16. Thus, in this embodiment, procedure control module 98 is configured to control contrast injection, image capture and percutaneous device movement in an intuitive manner via interaction by the user with a single control associated with the percutaneous device. This eliminates the need for the user to independently and separately actuate a separate control to trigger contrast media injection or image capture prior to percutaneous device movement.

In another embodiment the medical imaging system interacts with the robotic catheter procedure system and a targeting system to limit the x-rays from the imaging system to the immediate vicinity of a selected portion of the percutaneous device as it moves within the patient thereby reducing the x-ray exposure of the patient from that typical without such targeting. The targeting system may be instructed where to allow the x-rays to hit in any of a number of ways. The user may instruct the targeting system by using the display provided by the medical imaging system The targeting system may system may allow the x-rays to hit only the immediate vicinity of the leading edge of the percutaneous device controlled by the bedside system of the robotic catheter procedure system by recognizing the leading edge in the image provided by the medical imaging system. The targeting system may allow the x-rays to hit only the immediate vicinity of the leading edge of the percutaneous device controlled by the bedside system of the robotic catheter procedure system in response to a signal emitted by the leading edge. Or the targeting system may allow the x-rays to hit only the immediate vicinity of the leading edge of the percutaneous device controlled by the bedside system of the robotic catheter procedure system in response to information provided to it by the bedside system.

The medical imaging system may initially provide a display of the selected portion of the percutaneous device within or about to enter the patient along with a display of other portions of the patient such as the path the device is expected to follow as it accomplishes its diagnostic or therapeutic goal. The user may then interact with this display to instruct the targeting system narrow the beam of incident x-rays of the medical imaging system to the immediate vicinity of the selected portion. The display may allow the user to zoom in on the image of the selected portion and this zooming action may then be used to instruct the targeting system. The user may interact with the display using an input device such as a mouse of a light pencil. The display may be presented on a touch screen and the user may direct the targeting system by touching the appropriate portion of the image on the touch screen. The user may repeatedly interact with the display to track the progress of the leading edge as it advances into the patient.

The targeting system may be configured or trained to recognize the leading edge of the percutaneous device and upon recognizing it in an image provided by the medical imaging system it may act to allow the incident X-rays of this system to hit only the immediate vicinity of the leading edge. The targeting system may be preloaded with images of leading edges which are likely to be encountered in the operation of a robotic catheter procedure system such as the leading end of a guide or working catheter or a guide wire. Or the targeting system may be equipped with a module that allows it to be trained by the user. In this case the user would direct the targeting system to recognize the particular leading edge appearing in a given image.

The targeting system may be instructed as to the location of the leading edge of the percutaneous device by the bedside system of the robotic catheter procedure system. The bedside system may have one or more sensors which detect the distance that it has advanced or retracted the percutaneous device into or out of the patient. For instance, if the device is a guide or working catheter or a guide wire the bedside system may have a sensor which detects the distance forward into the patient or the distance backward out of the patient it has moved the catheter or guide wire.

The targeting system may be instructed as to the location of the leading edge of the percutaneous device by a signal emanating from this leading edge. The leading edge may be associated with a radio frequency (RF) tag which is probed by the targeting system. In this case an RF generator and an RF detector would be part of the targeting system. The leading edge may emit radiation of a particular frequency which is distinguishable from the X-rays of the medical imaging system. Or the leading edge may emit a magnetic signal. For instance, it may have been magnetized.

The medical imaging system may be a fluoroscopic system that comprises an X-ray emitter spatially separated from an X-ray detector such that the patient is placed between them. For instance it may have the C arm structure 32 illustrated in FIG. 1. The targeting system may direct the movement of the emitter, the detector or both to cause the X-rays to be limited to the immediate vicinity of a selected portion of the precutaneous device. Alternatively the patient 21 may be on a moveable support whose motion is directed by the targeting system. In such a case the bedside 12 would be attached to the moveable support to preserve its orientation to the patient 21 when the targeting system causes the support to move. The targeting system may also direct both the C arm and the support to move in order to cause the X-rays to be limited to the immediate vicinity of a selected portion of the precutaneous device. The emitter of the fluoroscopic system may have a shutter which limits the beam of radiation traveling between the emitter and the detector in response to instructions from the targeting system. This shutter may be adjustable so that it limits the beam to different portions of the patient as instructed by the targeting system. Such an adjustable shutter is described in U.S. Published Patent Application 2011/0075805 which is incorporated herein by reference.

The targeting system facilitates the operation of the bedside system 12 illustrated in FIG. 1 while reducing the X-ray exposure of the patient 21. The procedure involves advancing the percutaneous device into the patient with the robotic catheter procedure system, displaying the location of the percutaneous device within the patient on the display 26 or 28 and limiting the x-rays from the emitter of the medical imaging system 32 to the immediate vicinity of the leading edge of the percutaneous device as it moves within the patient. In one embodiment the display is a touch screen visible to the user of the robotic catheter procedure system, the imaging system displays a substantial portion of the path the percutaneous device is expected to follow as it advances into the patient and the user interacts with the touch screen to limit the x-rays to immediate vicinity of the leading edge of the percutaneous device as the device advances into the patient.

Further modifications and alternative embodiments of various aspects will be apparent to those skilled in the art in view of this description. Accordingly, this description is to be construed as illustrative only. The construction and arrangements, shown in the various exemplary embodiments, are illustrative only. While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be used alone or in combination with any of the features, elements, or components of any of the other embodiments discussed above. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A system comprising:

a bedside actuating mechanism configured to engage and to move a percutaneous device within a patient;

a user interface;

a sensor configured to detect a presence of a user's hand adjacent the user interface and generate a first input in response to detecting the presence of the user's hand, the first input indicating that movement of the percutaneous device is to occur; and a controller configured to determine that movement of the percutaneous device within the patient is to occur based on the first input, and automatically initiate capture of medical images of the patient by a medical imaging system in response to determining that the movement of the percutaneous device within the patient is to occur based on the first input.

2. The system of claim 1, wherein the controller is configured to initiate the capture of medical images prior to the movement of the percutaneous device.

3. The system of claim 1, wherein the user interface is configured to detect a second input; and the controller is configured to cause the percutaneous device to move within the patient based on the second input, the second input being subsequent to the first input.

4. The system of claim 1, wherein the controller is configured to determine that the movement of the percutaneous device has ceased, and stop the capture of medical images by the medical imaging system in response to determining that the movement of the percutaneous device has ceased.

5. The system of claim 4, further comprising:
a display device configured to display the medical images captured by the medical imaging system.

6. The system of claim 5, wherein the controller is configured to cause the display device to continuously display a last medical image captured by the medical imaging system after the capture of medical images has stopped.

7. The system of claim 1, wherein the controller is configured to control the movement of the percutaneous device via the bedside actuating mechanism.

8. The system of claim 7, wherein the controller is configured to control the movement of the percutaneous device and actuation of the medical imaging system based on user interaction with a single control.

9. The system of claim 1, wherein the controller is configured to automatically initiate the capture of medical images by the medical imaging system without requiring user interaction with a control specific to the medical imaging system.

10. The system of claim 1, further comprising:
the medical imaging system, wherein
the medical imaging system includes an x-ray source configured to emit x-rays toward the patient, and
the controller is configured to
identify a leading edge of the percutaneous device in the medical images captured by the medical imaging system, and
limit the x-rays from the x-ray source to an immediate vicinity of the leading edge of the percutaneous device as the percutaneous device moves within the patient, wherein
identification of the leading edge by the controller is based on loaded images of leading edges of percutaneous devices or training of the controller by a user.

11. The system of claim 1, further comprising:
one or more sensors configured to detect a distance that the percutaneous device has advanced into, or retracted out of, the patient.

12. The system of claim 1, further comprising:
the medical imaging system configured to capture the medical images of the patient.

13. A system comprising:
a bedside actuating mechanism configured to engage and to move a percutaneous device within a patient;
a user control positioned within an activation zone when in a resting position, the user control being configured to control initiation of capture of medical images of the patient by a medical imaging system when within the activation zone and configured to control movement of the percutaneous device within the patient when outside the activation zone;
a sensor configured to detect a presence of a user's hand adjacent the user control and generate a signal in response to detecting the presence of the user's hand; and
a controller configured to, in response to movement of the user control within the activation zone, automatically initiate the capture of medical images of the patient by the medical imaging system without causing movement of the percutaneous device within the patient, wherein movement of the user control displaces the user control from the resting position and a size of the activation zone is configurable,
the controller is further configured to cause the movement of the percutaneous device to stop in response to the user control returning to the resting position, and
the controller is further configured to cause the capture of medical images to stop in response to the signal indicating that the user's hand has exited the activation zone.

14. The system of claim 13, wherein the controller is configured to cause the movement of the percutaneous device in response to movement of the user control outside of the activation zone.

15. The system of claim 13, wherein the movement of the user control within the activation zone is indicative of an upcoming movement of the percutaneous device within the patient.

16. The system of claim 13, further comprising:
the medical imaging system configured to capture the medical images of the patient.

17. A system comprising:
a bedside actuating mechanism configured to engage and to move a percutaneous device within a patient;
a medical imaging system configured to capture and display medical images of the patient;
a user interface;
a sensor configured to detect a presence of a user's hand adjacent the user interface and generate a first input in response to detecting the presence of the user's hand, the first input indicating that movement of the percutaneous device is to occur;
a user control; and
a controller configured to
determine that movement of the percutaneous device within the patient is to occur based on the first input,
automatically initiate the capture and display of medical images by the medical imaging system in response to determining that movement of the percutaneous device within the patient is to occur based on the first input, and
cause movement of the percutaneous device based on the movement of the user control after initiation of the capture and display of medical images by the medical imaging system.

18. The system of claim 17, wherein the controller is configured to
output a first control signal to the medical imaging system to automatically initiate the capture and display of medical images, and
output a second control signal to the bedside actuating mechanism to cause the movement of the percutaneous device in response to an indication from the medical imaging system that the capture and display of medical images has been initiated.

19. The system of claim 17, wherein the controller is configured to
determine that the movement of the percutaneous device within the patient is to occur by predicting a next movement of the percutaneous device based on a pattern of use of the user control, and
automatically initiate the capture and display of medical images by the medical imaging system based on the predicted next movement.

20. A robotic catheter procedure system comprising:
a bedside system including an actuating mechanism, the actuating mechanism configured to engage and to impart movement to a percutaneous device within a patient; and a controller coupled to the bedside system, a medical imaging system, and a user input system, the controller configured to determine that movement of the percutaneous device within the patient is to occur based on a first input received from a sensor, the first input indicating a presence of a user's hand adjacent to a user interface, automatically initiate capture of medical images by the medical imaging system in response to determining that movement of the percutaneous device within the patient is to occur, and cause movement of the percutaneous device via the bedside system based on a signal received from the user input system and only after initiation of the capture of medical images by the medical imaging system.

21. The robotic catheter procedure system of claim 20, wherein the controller is configured to determine that image capture has been initiated based on a signal from the medical imaging system indicating that image capture has been initiated.

22. The robotic catheter procedure system of claim 20, wherein the medical imaging system includes a digital x-ray imaging device.

23. The robotic catheter procedure system of claim 20, wherein the controller is configured to communicate with a contrast injection system.

24. The robotic catheter procedure system of claim 20, wherein the actuating mechanism is a guide wire actuating mechanism, a working catheter actuating mechanism, or a guide catheter actuating mechanism.

25. The robotic catheter procedure system of claim 20, wherein the actuating mechanism includes a guide wire actuating mechanism, a working catheter actuating mechanism, and a guide catheter actuating mechanism.

26. The robotic catheter procedure system of claim 25, wherein the bedside system comprises:

a cassette including the actuating mechanism.

27. The robotic catheter procedure system of claim 25, wherein the guide wire actuating mechanism includes a rotational actuator.

28. The robotic catheter procedure system of claim 25, wherein the working catheter actuating mechanism includes a rotational actuator.

29. The robotic catheter procedure system of claim 20, wherein the controller is configured to output a first control signal to the medical imaging system to automatically initiate the capture of medical images, and output a second control signal to the actuating mechanism to cause the movement of the percutaneous device in response to an indication from the medical imaging system that the capture of medical images has been initiated.

* * * * *